United States Patent [19]

Szonntagh

[11] 4,276,913
[45] Jul. 7, 1981

[54] METHOD AND APPARATUS FOR FLUID SAMPLE INJECTION FOR FLUID CHROMATOGRAPHY

[75] Inventor: Eugene L. Szonntagh, Flourtown, Pa.

[73] Assignee: Honeywell Inc., Minneapolis, Minn.

[21] Appl. No.: 81,629

[22] Filed: Oct. 4, 1979

[51] Int. Cl.³ ............................................. B65B 3/04
[52] U.S. Cl. .................................. 141/1; 23/232 C; 73/864.81
[58] Field of Search ............................ 141/1, 392, 98; 73/422 GC; 23/232 C

[56] References Cited
U.S. PATENT DOCUMENTS
4,199,988  4/1980  Riegger .......................... 73/422 GC Primary Examiner—Houston S. Bell, Jr.
Attorney, Agent, or Firm—Laurence J. Marhoefer; Lockwood D. Burton; Mitchell J. Halista

[57] ABSTRACT

A method and apparatus for fluid sample injection for a chromatograph using an acoustic or sonic generator generating standing waves in a hollow tube. A selectively controlled source of a carrier fluid is arranged to apply a carrier fluid to one end of the tube. A source of sample fluid is connected by a valve to a predetermined location along the tube corresponding to the location of a node separation space in a standing wave generated by the acoustic signal generator. A sample exit port is located on the other side of the hollow tube and is controlled by a valve to provide an exit for the sample fluid flowing across the hollow tube between the nodes. Another end of the tube that is connected to a chromatographic column to supply the sample thereto for separation and subsequent application to a chromatographic detector. A timing and control circuit is used to control the frequency and amplitude of the acoustic signal generator and the timing of the operation of the carrier gas and sample control valves.

18 Claims, 1 Drawing Figure

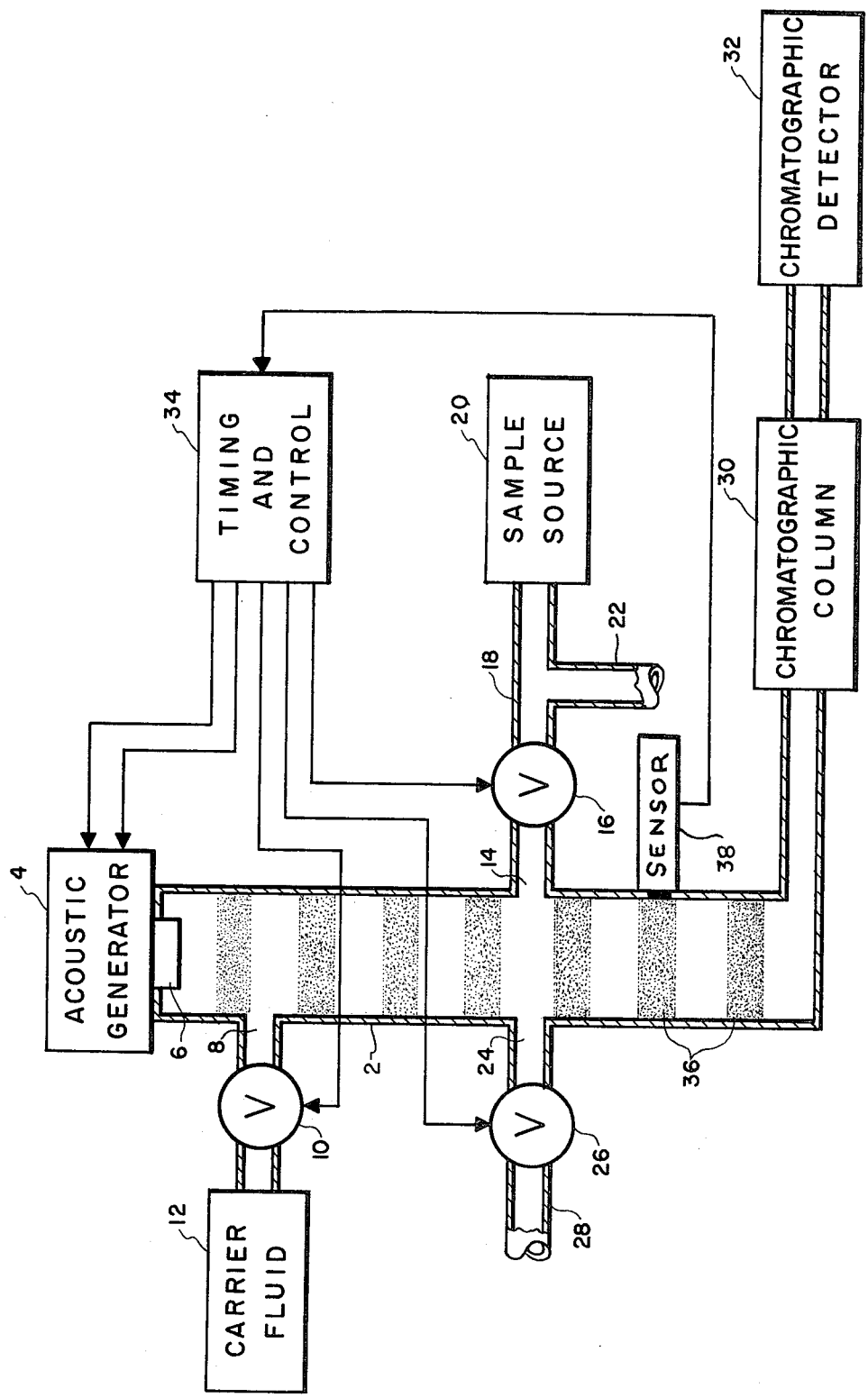

4,276,913

METHOD AND APPARATUS FOR FLUID SAMPLE INJECTION FOR FLUID CHROMATOGRAPHY

BACKGROUND OF THE INVENTION

1. Field of the Invention

The present invention relates to chromatographic analyzers. More specifically, the present invention is directed to a sample injection apparatus for a chromatographic analyzer.

2. Description of the Prior Art

The use of chromatographic analyzers for analyzing fluid samples, e.g., gas mixtures, is well-known in the art. A sample injection means is used for selectively injecting a sample of the gas to be analyzed into a carrier fluid stream to be carried to the chromatographic separating column. The purpose of the sample injector is two-fold, i.e., it must inject a sample into the carrier fluid stream and it must provide a means for predetermining the volume of the sample to be injected. The prior art sample injection devices have included mechanically operated syringes, e.g., U.S. Pat. Nos. 3,940,995 and 3,985,166, valves having internal storage loops, e.g., U.S. Pat. Nos. 3,787,026 and 3,975,946 and other complicated mechanical devices which have usually been unable to provide long term reliability in combination with a low manufacturing cost. Accordingly, it would be desirable to provide a sample injection apparatus capable of having extremely long operating life as well as a simple and inexpensive structure.

SUMMARY OF THE INVENTION

An object of the present invention is to provide an improved chromatographic sample injection apparatus.

In accomplishing this and other objects, there has been provided, in accordance with the present invention, a sample injection apparatus having an acoustic signal generator at one end of a closed chamber adjacent to a selectively controlled source of a carrier fluid supplying the interior volume of the chamber. A selectively controlled source of the sample to be analyzed is arranged to supply the sample at a point within the chamber aligned with the space between the nodes of the standing acoustic waves generated within the chamber by the acoustic signal generator.

BRIEF DESCRIPTION OF THE DRAWING

A better understanding of the present invention may be had from the following detailed description is read in connection with the accompanying drawing, which the single FIGURE is an illustration of an example of a sample injection apparatus embodying the present invention.

DESCRIPTION OF THE PREFERRED EMBODIMENT

Referring to the single FIGURE drawing in more detail, there is shown a diagrammatic illustration of a sample injection apparatus having a hollow-chamber in the form of a cylindrical tube 2 with an acoustic signal generator 4 located at one end thereof. An acoustic signal output device 6 driven by the single generator 4 is located within the hollow tube 2 at the aforesaid end thereof. The acoustic signal producing means 6 may be any suitable device such as a piezoelectric element capable of producing acoustic signals when suitably driven by an electrical signal, such devices being well-known in the art. Adjacent to the end of the tube having the acoustic signal output device 6 attached thereto is a first fluid inlet port 8. The term fluid as used herein refers to either a liquid or a gaseous fluid since the sample injection apparatus of the present invention is useable with either fluid medium. The inlet port 8 is connected to the output of an electrically controlled fluid valve 10. The inlet of the valve 10 is connected to a source of the carrier fluid 12.

At a suitable distance along the tube 2, as determined by the presence of the nodes of a standing wave within the tube 2, as discussed more fully hereinafter, is located at a second inlet port 14. A second selectively controlled fluid valve 16 has its output connected to the port 14 and its input connected to a fluid sample conduit 18 extending between the valve 16 and a source of a sample to be analyzed 20. A first fluid exhaust port 22 is connected to the conduit 18 between the valve 16 and the source 20. A fluid outlet port 24 is located in the wall of the tube 2 opposite to the second inlet port 14. A third selectively controlled fluid valve 26 has its input connected to the output port 24 and its output connected to a fluid exhaust conduit 28. The other end of the tube 2 is connected to the input of a chromatographic separating column 30, such devices being well-known in the art. A chromatographic detector 32 is connected to the output of the column 30. A timing and control means 34 is used to control the frequency and output energy level of the acoustic generator 4 and single producing means 6 and the selective operation of the fluid valves 10, 16 and 26.

In operation, the sample injection apparatus of the present invention is used to measure a sample volume and to inject, or transport, that volume of the sample to be analyzed to the chromatographic column 30. In order to determine the volume of the sample to be provided, the frequency of the acoustic generator is adjusted by the timing and control circuit 34 to produce a frequency output which is suitable for producing standing waves having nodes 36 separated by the desired spacing to produce the sample volume, e.g., a 150 Kilohertz frequency would product acoustic nodes 1 millimeter apart in air. Further, while the tube 2 is shown in an enlarged form for purposes of illustration, and actual tube may have an internal diameter of only several millimeters, e.g., 10 mm, and a commensurate length, e.g., 100 mm. The location of the sample injection port 14 and sample exit port 24 is predetermined to coincide with the location of the aforesaid sample volume determined by the position of the space between two adjacent nodes in the standing waves produced by the acoustic signal from the acoustic generator 4, i.e., an antinode.

During this initial phase of the operation of the injection apparatus, the valves 10, 16, and 24 are closed by the timing and control circuit 34. After the acoustic signal has been established within the column 2, the sample injection port control valve 16 and the sample exit port control valve 26 are opened by the timing and control circuit 34. This open state of the valves 16 and 26 allows the sample from the sample source 20 to flow through the fluid conduit 18 past the valve 16 into the inlet port 14. The sample continues across the space between the nodes of the standing waves in the hollow tube 2 into the exit port 24 and exits via the via exit valve 26 and the fluid exhaust conduit 28. After a predetermined period of time, the nodes and the volume therebetween having the sample flowing therethrough will be saturated by the sample. At this time, the valves 16 and 26 are closed by the timing and control circuit 34 to trap the sample of the sample fluid to be analyzed between the nodes within the column 2. Subsequently, the carrier gas control valve 10 is opened by the timing and control circuit 34. The carrier fluid from the carrier fluid source 12 is then allowed to enter the column 2 and to sweep the sample of the fluid to be analyzed which is present within the column 2 into the chromatographic column 30 for separating and into the chromatographic detector 32.

A further enhancement of operation during the transportation to the sample by the carrier gas 12 may be effected by the timing control circuit 34 to reduce the acoustic energy from the acoustic generator 4 and signal producing device 6 to prevent any possible interference with the transportation of the sample by the carrier fluid 12 into the chromatographic column 30. Thus, in this latter type of operation, the sonic energy would be elevated during the trapping phase of the sample between the standing wave nodes and subsequently reduced when the carrier gas is introduced into the column 2. In either type of operation, the sonic energy during the sample trapping phase should be high enough to prevent the sample fluid from migrating past the standing wave nodes within the column 2. Further, it should be noted that the size of the sample may be discretely vaired by varying the acoustic frequency by an adjustment of the acoustic generator 4 by the timing and control circuit 34. Additionally, a pressure sensor 38 may be mounted on the column 2 to project therethrough to sense the internal pressures representative of the nodes 36. An output signal from the sensor 38 would be applied to the control circuit 34 to effect a requisite frequency control of the acoustic generator 4 to ensure a proper location of the nodes 36 with respect to the ports 14 and 24.

Accordingly, it may be seen that there has been shown, in accordance with the present invention, an improved sample injection apparatus.

The embodiments of the invention in which an exclusive property or privilege is claimed are defined as follows:

1. A fluid sample injection apparatus comprising
   a hollow tube,
   an acoustic signal generator located at one end of said hollow tube and arranged to produce acoustic standing waves within said hollow tube,
   a sample inlet port located in a wall of said hollow tube and spaced from said acoustic signal generator means,
   a fluid sample outlet port located in said wall of said tube across from said fluid inlet port,
   valve means for selectively connecting said fluid inlet port to a source of a sample to be analyzed,
   second valve means for selectively connecting said exit port to a fluid exhaust, and
   timing means for periodically and concurrently operating said first and second valve means.

2. A fluid injection apparatus as set forth in claim 1 and including a carrier fluid inlet port arranged in said wall of said hollow tube between said acoustic signal generator means and said sample inlet and exit ports, a third valve means arranged to connect said carrier fluid port to a source of a carrier fluid, said timing means being arranged to selectively control said third valve means between the operation of said first and second valve means.

3. A fluid injection apparatus as set forth in claim 2 and further including a fluid separating and detecting means connected to the other end of said hollow tube.

4. A fluid injection apparatus as set forth in claim 2 wherein said timing means is arranged to control the energy of an acoustical signal from said acoustic signal operating means between a first and a second acoustic signal energy level during the operation of said carrier fluid valve means and said first and second valve means, respectively.

5. A fluid injection apparatus as set forth in claim 4 wherein said first acoustic signal energy level is higher than said second acoustic signal energy level.

6. A method of injecting a fluid sample comprising the steps of producing an acoustic standing wave in a closed chamber, introducing a fluid sample between two adjacent nodes of the standing waves, trapping the fluid sample between the nodes and ejecting the trapped fluid sample from the chamber.

7. A method as set forth in claim 6 and including the further step of admitting a carrier fluid into the chamber to eject the trapped fluid sample from the chamber.

8. A method as set forth in claim 6 and including the further step of reducing the acoustic energy of the acoustic wave to facilitate the ejecting of the trapped fluid sample.

9. A method as set forth in claim 7 and including the further step of reducing the acoustic energy of the acoustic wave after the admission of the carrier fluid.

10. A method as set forth in claim 6 and including the further steps of separating and detecting the components of the fluid sample ejected from the chamber.

11. A fluid sample injection apparatus comprising
    a closed chamber,
    acoustic signal generating means for producing acoustic standing waves in said chamber,
    fluid sample admitting means for introducing and trapping a fluid sample between two adjacent nodes of said standing wave, and
    means for ejecting said trapped fluid sample from said closed chamber.

12. A fluid sample injection apparatus as set forth in claim 11 wherein said last-mentioned means includes carrier fluid admitting means arranged to selectively connect said chamber to a source of a carrier fluid after said trapping of said fluid sample.

13. A combination comprising
    a hollow chamber,
    acoustic signal generating means for generating standing acoustic waves in said chamber and
    fluid sample injection means for introducing a fluid sample between nodes of said standing acoustic waves.

14. A combination as set forth in claim 13 and further including means for injecting a carrier fluid into said chamber to urge a flow of said fluid sample toward a predetermined point in a wall of said chamber and a fluid sample exhaust port located at said predetermined point.

15. A combination as set forth in claim 13 wherein said chamber is a hollow tube, said generating means being located at one end of said tube and said sample injection means being located in a wall of said tube spaced from said generating means.

16. A combination as set forth in claim 15 and further including a carrier fluid injecting means for injecting a carrier fluid into said tube and being located in a wall of said tube between said generating means and said sample injection means.

17. A combination as set forth in claim 16 and further including a fluid exhaust port located at the opposite end of said tube from said signal generating means.

18. A combination as set forth in claim 16 and further including a timing means for controlling the operation of said fluid sample injection means and said carrier fluid injection means to produce an alternate operation of said fluid sample injection means and said carrier fluid whereby said carrier fluid is injected into said tube between the introductions of the fluid sample by said fluid sample injection means.

* * * * *